United States Patent [19]

Morais

[11] Patent Number: 4,786,253
[45] Date of Patent: Nov. 22, 1988

[54] DENTAL MODEL ARTICULATOR

[75] Inventor: Filipe M. L. Morais, Johannesburg, South Africa

[73] Assignee: Henneret Properties (Proprietary) Limited, Vereeniging, South Africa

[21] Appl. No.: 23,720

[22] Filed: Mar. 9, 1987

[51] Int. Cl.[4] ............................................. A61C 11/00
[52] U.S. Cl. ........................................ 433/60; 433/64
[58] Field of Search ............................ 433/54, 60, 64

[56] References Cited

U.S. PATENT DOCUMENTS 3,823,476 7/1974 Hudson et al. .................... 433/54
4,207,677 6/1980 Lampert ............................ 433/54
4,533,323 8/1985 Hoffman ........................... 433/60

Primary Examiner—Robert Peshock
Attorney, Agent, or Firm—Dressler, Goldsmith, Shore, Sutker & Milnamow, Ltd.

[57] ABSTRACT

A dental model articulator 10, intended for use with a dental model 12 comprising a cast of a set of upper teeth, and a case of a set of lower teeth, comprises two parts 18 and 20 which are constituted by a strip 22 of a resiliently flexible material. The strip 22 has a region of reduced thickness to form a flexible hinge 26 about which the parts 18 and 20 can hinge flexibly relative to each other. Each part 18, 20 has a boss 34 formed integrally therewith, each boss 34 defining a socket 36. A pair of attachment means 28, comprising a substantially spherical member 30 with a spigot-like formation 32 projecting therefrom is provided. The spigot-like formations 32 are insertable into the sockets 36 of the bosses 34. Each attachment means 28 is attachable to one of the casts to enable a user of the articulator 10 to manipulate the casts pivotally and laterally with respect to each other to correlate the casts.

9 Claims, 2 Drawing Sheets

DENTAL MODEL ARTICULATOR

FIELD OF THE INVENTION

This Invention relates to a dental device. More particularly, the invention relates to a dental articulator for use with a dental model comprising casts of a set of upper teeth and a set of lower teeth of a person.

BACKGROUND OF THE INVENTION

The Applicant is aware of U.S. Pat. Nos. 4,382,787, 4,449,930, 4,533,323 and 4,548,581 as well as U.S. Pat. Nos. Des. 286,179 and 286,436, all to Huffman. These patents and design patents describe and illustrate various embodiments of dental model articulators. All of the articulators described and illustrated in these patents and design patents comprise a pair of substantially U-shaped brackets which have their limbs pivotally interconnected. In some of the illustrated embodiments, the limbs of the U-shaped brackets are interconnected, snap-fit fashion. Substantially spherical members are formed integrally with crosspieces of each of the U-shaped brackets. A mounting member is provided for attachment to each cast. Each mounting member defines a socket in a rear portion thereof within which the spherical member of one of the brackets fits to form a ball and socket joint.

It is a problem with this type of arrangement, that two adhesive bonds have to be formed for each cast, ie. bonding of the mounting member to the cast, and the bonding of the spherical member in the socket. While waiting for these adhesive bonds to set, the casts together with the articulator, have to be held and due to the use of the two adhesive bonds for each cast, the likelihood of the position of the articulator relative to the casts moving during the setting of the adhesive bonds is increased. Also, with the provision of the snap-fit type interconnection between the limbs of the brackets, lateral movement, without these snap-fit interconnections coming apart, is limited.

The Applicant is further aware of apparatus for locating a cast of a set of upper teeth and a cast of a set of lower teeth of a dental model in an operative configuration which simulates the relative position of the upper and lower sets of teeth of a person, which comprises a retort stand type arrangement having two vertically spaced, horizontally extending arms which are releasably clamped to a vertical bar of the retort stand. The arms are articulated to be pivotal in a vertical plane. With this arrangement, the two casts of the model are initially waxed together, and then are cemented to the respective free ends of the arms eg. by using Plaster of Paris. Once the cement has set, the two casts of the model, still waxed together and with the arms attached, are released from the retort stand. The two casts are then separated from each other by removing the wax. Finally the arms are again clamped to the stand and the pivotal opening and closing movement of a person's jaws can be simulated by pivoting the arms relative to each other. It will be appreciated that this is a time consuming an somewhat messy process and a technician usually requires assistance, albeit unskilled assistance to carry it out. Also, with this type of apparatus only pivotal movement of a person's jaw can be simulated, ie. no lateral movement of the jaw can be simulated.

SUMMARY OF THE INVENTION

According to the invention, there is provided a dental articulator for use with a dental model comprising casts of a set of upper teeth and a set of lower teeth of a person, the articulator including a strip of flexible material having a region of reduced thickness extending across the strip to divide the strip into two parts, the parts being flexible relative to each other about the region of reduced thickness; and an attachment means releasably secured to an end of each part remote from the region of reduced thickness of the strip, each attachment means being attachable to one of the casts to enable a user of the articulator to manipulate the casts pivotally and laterally with respect to each other to correlate the casts.

The strip may be of a substantially elongate rhombic shape having truncated ends, the region of reduced thickness extending across the minor axis of the strip so that the two parts of the strip are substantially uniform.

The strip may be of a synthetic plastics material. The synthetic plastics material may be polypropylene or polyethylene.

Each attachment means may include a substantially spherical member having a spigot-like formation projecting from the spherical member at an angle to the member.

Each part may include a boss arranged at the end of the part remote from the region of reduced thickness the boss defining a socket to accommodate the spigot-like formation of the attachment means.

The spigot-like formation of each attachment means may include a rib extending about at least a portion of the circumference thereof, the rib being engageable with a complementary recess of the socket to provide the releasable securing of the attachment means to its associated part.

Each boss may be formed integrally with its associated part as a one-piece unit.

The invention extends also to a dental articulator for use with a dental model comprising casts of a set of upper teeth and a set of lower teeth of a person, the articulator including a strip of a flexible material having a region of reduced thickness extending across the strip to divide the strip into two parts, the parts being flexible relative to each other about the region of reduced thickness, each part including a boss, defining a socket, arranged at the end of the part remote from the region of reduced thickness of the strip; and a pair of attachment means releasably secured to each of the parts, each attachment means comprising a substantially spherical portion with a spigot-like formation projecting from the spherical portion, the spigot-like formation of one attachment means being receivable in the socket of one of the bosses and the spigot-like formation of the other attachment means being receivable in the socket of the other boss, the attachment means being attachable to the casts to enable a user of the articulator to manipulate the casts pivotally and laterally with respect to each other.

The invention extends still further to a method of correlating a pair of casts of a detail model, the pair of casts comprising a cast of a set of upper teeth and a cast of a set of lower teeth of a person, the method including forming a substantially semi-spherical cavity in a rear surface of each cast;

releasably securing an attachment means to each part of a dental articulator, the two parts of the dental articulator being constituted by a strip of a flexible material having a region of reduced thickness extending across the strip to render the two parts flexible relative to each other about the region of reduced thickness;

inserting a substantially spherical portion of each attachment means into the cavities of each cast to form a ball and socket joint;

adjusting the position of the casts relative to each other to adjust registration of the sets of teeth; and immobilizing the ball and socket joint formed between each cast and its associated attachment means.

BRIEF DESCRIPTION OF THE INVENTION

The invention is now described by way of example with reference to the accompanying diagrammatic drawings.

DETAILED DESCRIPTION OF THE DRAWINGS

Figure 1:
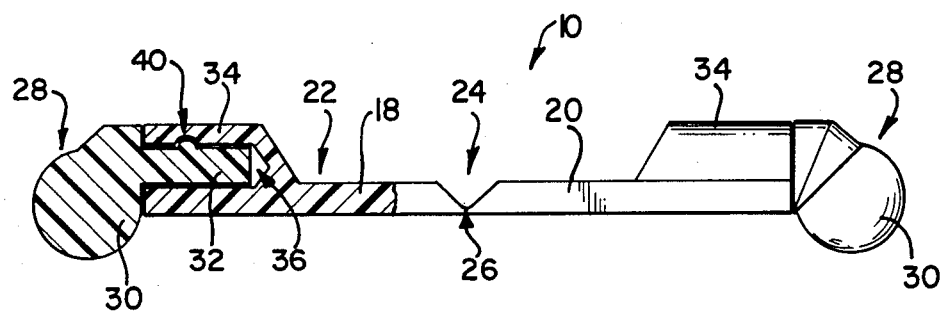
FIG. 1 shows a part-sectional side elevation of a dental articulator in accordance with the invention.
Figure 2:
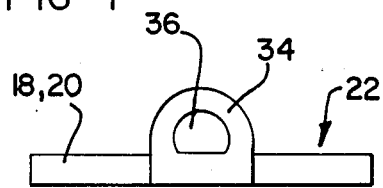
FIG. 2 shows an end elevation of a part of the dental articulator of FIG. 1, with attachment means of the articulator omitted.
Figure 3:
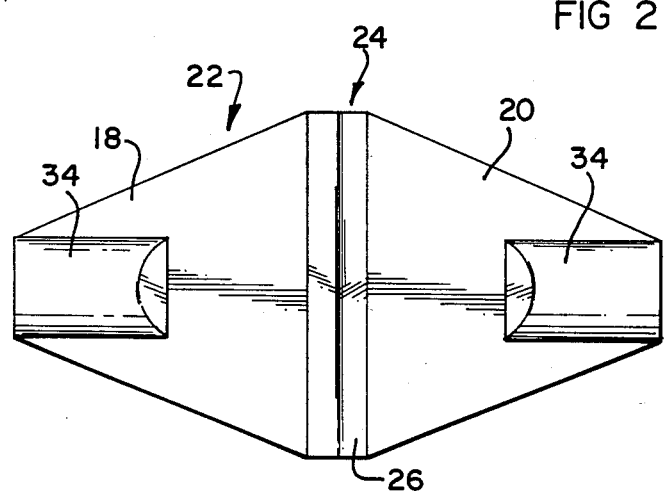
FIG. 3 shows a plan view of the articulator of FIG. 1 with the attachment means omitted.
Figure 4:
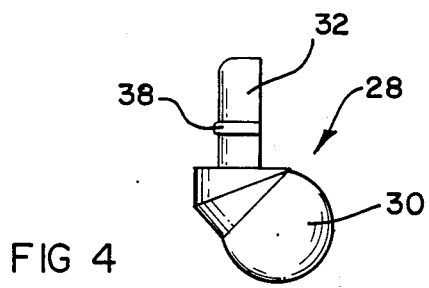
FIG. 4 shows a side view of an attachment means forming part of the articulator.
Figure 5:
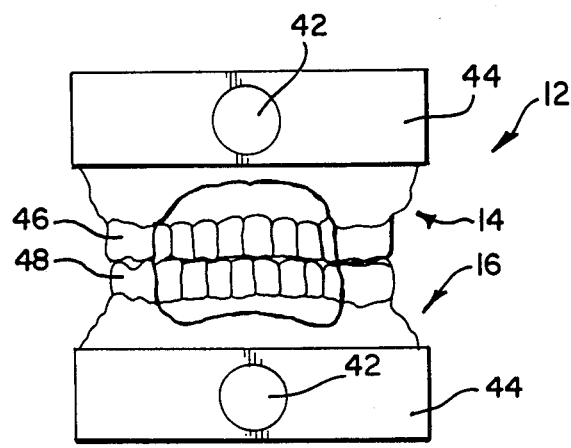
FIG. 5 shows a rear view of a dental model with which the dental articulator of FIG. 1 is used.
Figure 6:
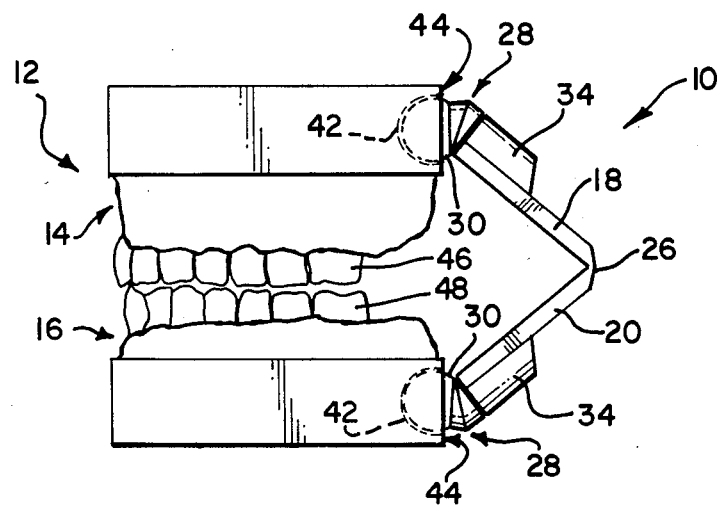
FIG. 6 shows a side view of the dental articulator of FIG. 1 in use with a dental model as shown in FIG. 5.

Referring to the drawings, a dental articulator in accordance with the invention is designated generally by the reference numeral 10. The dental articulator 10 is intended for use with a dental model 12 (FIGS. 5 and 6), the dental model 12 comprising a cast 14 of a set of upper teeth, and a cast 16 of a set of lower teeth.

The dental articulator 10 comprises two parts 18 and 20 which are constituted by a strip 22 of a resiliently flexible material. The strip 22 has a region of reduced thickness 24 extending across the strip 22 to divide the strip 22 into the two parts 18 and 20, and to form a flexible hinge 26 about which the parts 18 and 20 can hinge flexibly relative to each other.

An attachment means 28, is releasably securable to an end of each part 18, 20 remote from the flexible hinge 26. Each attachment means 28 is attachable to one of the casts 14, 16 to enable a user of the articulator 10 manipulate the casts 14, 16 pivotally and laterally with respect to each other to correlate the casts 14,16.

The strip 22 is of a substantially elongate rhombic shape having truncated ends. The flexible hinge 26 extends across the minor axis of the strip so that the two parts 18 and 20 of the strip 22 are substantially uniform in shape and configuration.

The strip 22 is of a synthetic plastics material, such as polypropylene, polyethylene, or the like.

Each attachment means 28 includes a substantially spherical member 30 having a spigot-like formation 32 projecting at an angle from the spherical member 30. The spigot-like formation 32 projects at an angle of about 45° to the spherical member 30.

Each part 18 and 20 includes a boss 34 arranged at the end of the part 18, 20 remote from the flexible hinge 26.

Each boss 34 defines a socket 36 to accommodate the spigot-like formation 32 of the attachment means 28.

The spigot-like formation 32 of each attachment means 28 includes a rib 38 extending about a portion of the circumference of the spigot-like formation 32. The rib 38 is engageable with a complementary recess 40 of the socket 36 of the boss 34, so that the spigot-like formation 32 is a snap fit within the socket 36 of the boss 34.

In use, substantially semi-spherical cavities 42 are formed in a rear surface 44 of each of the casts 14, 16 of the dental model 12. The cavities 42 are of a size to receive the spheres 30 of the attachment means 28 snugly therein. The spigot-like formation 32 of each attachment means 28 is then inserted into the socket 36 of its associated boss 34.

A quick-setting adhesive material is applied to the interior surfaces of the cavities 42 as well as to the surfaces of the spheres 30 of the attachment means 28. The casts 14 and 16 of the model 12 are held in an operative position in which they simulate the bite of a person's jaw, and while being held in this position, the spheres 30 are inserted into the cavities 42. The casts 14 and 16 are retained in this position until the adhesive material has set.

Thereafter, the first and second parts 18 and 20 of the dental articulator 10 are pivoted with respect to each other about the hinge 26 to simulate the opening and closing of the jaws of a person. Further, the parts 18 and 20 can be displaced laterally with respect to each other to displace the casts 14 and 16 of the model 12 laterally with respect to each other to simulate lateral movement of the jaws of a person.

This enables a user of the articulator 10 rapidly to ascertain the registration of teeth 46 and 48 of the casts 14 and 16 respectively, and to make the necessary adjustments to ensure proper registration of the teeth 46 and 48.

I claim:

1. A detail model articulator for use with a dental model comprising casts of a set of upper teeth and a set of lower teeth of a person, the articulator including a strip of a flexible material having a region of reduced thickness extending across the strip to divide the strip into two parts, the parts being flexible relative to each other about the region of region thickness; and an attachment means releasably secured to an end of each part remote from the region of reduced thickness of the strip, each attachment means comprising a substantially spherical member having a spigot-like formation being receivable in a socket at the said end of each part remote from the region of reduced thickness, each attachment means being attachable to one of the casts to enable a user of the articulator to manipulate the casts pivotally and laterally with respect to each other to correlate the casts.

2. An articulator as claimed in claim 1, in which the strip is of a substantially elongate rhombi shape having truncated ends, the region of reduced thickness extending across the minor axis of the strip so that the two parts of the strip are substantially uniform.

3. An articulator as claimed in claim 1, in which the strip is of a synthetic plastic material.

4. An articulator as claimed in claim 3, in which the synthetic plastics material is polypropylene or polyethylene.

5. An articulator as claimed in claim 1 in which the spigot-like formation of each attachment means projects from the spherical member at an angle to the member.

6. An articulator as claimed in claim 1, in which each part includes a boss arranged at the end of the part remote from the region of reduced thickness of the strip, the boss defining the socket within which the spigot-like formation of the attachment means is receivable.

7. An articulator as claimed in claim 6, in which the spigot-like formation of each attachment means includes a rib extending about at least a portion of the circumference thereof, the rib being engageable with a complementary recess of the socket to provide the releasable securing of the attachment means to its associated part.

8. An articulator as claimed in claim 6 in which each boss is formed integrally with its associated part as a one-piece unit.

9. A dental articulator for use with a dental model comprising casts of a set of upper teeth and a set of lower teeth of a person, the articulator including
- a strip of a flexible material having a region of reduced thickness extending across the strip to divide the strip into two parts, the parts being flexible relative to each other about the region of reduced thickness, each part including a boss, defining a socket, arranged at the end of the part remote from the region of reduced thickness of the strip; and
- a pair of attachment means releasably secured to each of the parts, each attachment means comprising a substantially spherical portion with a spigot-like formation projecting from the spherical portion, the spigot-like formation of one attachment means being receivable in the socket of one of the bosses and the spigot-like formation of the other attachment means being receivable in the socket of the other boss, the attachment means being attachable to the casts to enable a user of the articulator to manipulate the casts pivotally and laterally with respect to each other.

* * * * *